US012114935B2

(12) United States Patent
Coiseur et al.

(10) Patent No.: US 12,114,935 B2
(45) Date of Patent: Oct. 15, 2024

(54) ROBOTIC GUIDED 3D STRUCTURED LIGHT-BASED CAMERA

(71) Applicant: MedTech S.A., Montpellier (FR)

(72) Inventors: Florian Coiseur, Lattes (FR); Pierre Maillet, Saint Aunes (FR)

(73) Assignee: MedTech S.A., Montpellier (FR)

( * ) Notice: Subject to any disclaimer, the term of this patent is extended or adjusted under 35 U.S.C. 154(b) by 856 days.

(21) Appl. No.: 17/174,068

(22) Filed: Feb. 11, 2021

(65) Prior Publication Data

US 2021/0244485 A1 Aug. 12, 2021

Related U.S. Application Data

(60) Provisional application No. 62/975,469, filed on Feb. 12, 2020.

(51) Int. Cl.
| | |
|---|---|
| A61B 34/20 | (2016.01) |
| A61B 34/32 | (2016.01) |
| A61B 90/00 | (2016.01) |
| A61B 90/50 | (2016.01) |
| G16H 20/40 | (2018.01) |
| G16H 30/20 | (2018.01) |
| G16H 40/63 | (2018.01) |
| A61B 17/00 | (2006.01) |

(52) U.S. Cl.
CPC ............ *A61B 34/20* (2016.02); *A61B 34/32* (2016.02); *A61B 90/361* (2016.02); *A61B 90/50* (2016.02); *G16H 20/40* (2018.01); *G16H 30/20* (2018.01); *G16H 40/63* (2018.01); *A61B 2017/00725* (2013.01); *A61B 2034/2057* (2016.02); *A61B 2090/3612* (2016.02); *A61B 2090/364* (2016.02)

(58) Field of Classification Search
None
See application file for complete search history.

(56) References Cited

U.S. PATENT DOCUMENTS

| | | |
|---|---|---|
| 10,013,777 B2 | 7/2018 | Mariampillai et al. |
| 2012/0307027 A1 | 12/2012 | Popovic et al. |
| 2018/0235715 A1 | 8/2018 | Amiot et al. |
| 2019/0142524 A1 | 5/2019 | Hladio et al. |
| 2019/0199915 A1 | 6/2019 | Coiseur |
| 2020/0015923 A1 | 1/2020 | Scheib et al. |
| 2020/0078097 A1* | 3/2020 | Gregerson ............. B25J 9/1666 |

OTHER PUBLICATIONS

"European Application Serial No. 21156964.5, Extended European Search Report mailed Jul. 1, 2021", 11 pgs.
"European Application Serial No. 21156964.5, Response filed Jan. 28, 2022 to Extended European Search Report mailed Jul. 1, 2021", 23 pgs.

* cited by examiner

*Primary Examiner* — Leon Flores
(74) *Attorney, Agent, or Firm* — SCHWEGMAN LUNDBERG & WOESSNER, P.A.

(57) ABSTRACT

A system or method may be used to provide registration, calibration, or tracking of patient anatomy using a camera and a robotic surgical system. The camera may include a structured light camera. The camera may be used to acquire an image of patient anatomy or a reference object. A method may include determining a distance (e.g., from the camera) or a location of the patient anatomy or the reference object. The robotic surgical system may include a robotic arm that may be configured to move based on the distance or location of the patient anatomy or the reference object.

17 Claims, 13 Drawing Sheets

ROBOTIC GUIDED 3D STRUCTURED LIGHT-BASED CAMERA

CLAIM OF PRIORITY

This application claims the benefit of priority to U.S. Provisional Applications No. 62/975,469 filed Feb. 12, 2020, titled "Robotic Guided 3D Structured Light-Based Camera," which is hereby incorporated herein by reference in its entirety.

BACKGROUND

Computer-assisted surgery is a growing field that encompasses a wide range of devices, uses, procedures, and computing techniques, such as surgical navigation, pre-operative planning, and various robotic techniques. In computer-assisted surgery procedures, a tracking system is often used to register or track various objects, such as patient anatomy, instruments, robotic components, or the like. The tracking system may be used to register real patient space and image patient space. Typical techniques require point-based registration with landmarks or markers or 3D surface model registration, both via a probe. However, these techniques are imprecise or invasive.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
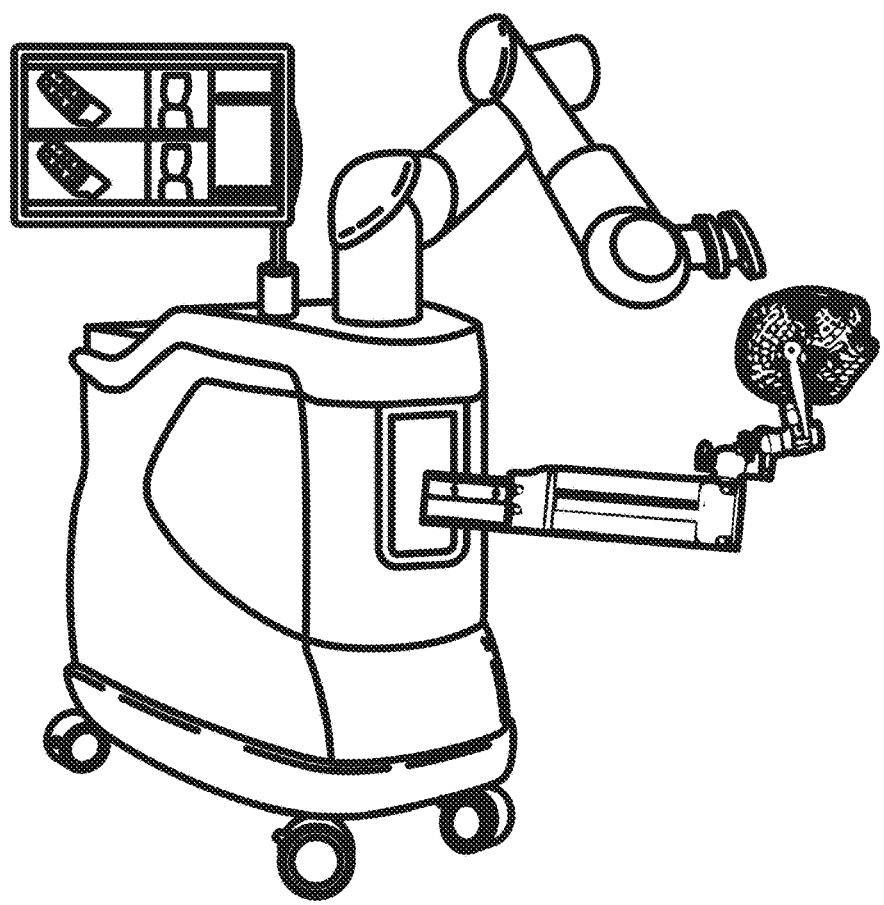
FIG. 1 illustrates a robotic surgical system in accordance with some embodiments.

Systems and methods for robotics surgeries and more particularly to the use of a camera affixed to an end effector of a robotic arm or embedded in a robotic arm for 3D image, target, or other acquisition, such as for registration, calibration, or tracking, are described herein. For example, the systems and methods may perform one or more tasks associated with robotic surgeries, such as registration between or among robot, real patient space, and medical imaging space, verification of robot calibration, tracking of patient anatomy, or the like. The systems and methods herein may provide fast, user friendly, intuitive, accurate, non-invasive, or contactless techniques for 3D acquisition of patient anatomy in order to perform registration between robot, patient, and medical imaging frames of reference.

Usage of the systems and methods described herein may include performing registration such as among a surgical robot, a patient and medical images, for example when a robotic surgical device is activated in a surgical setting, or at the beginning of a surgical procedure. Registration techniques described herein may replace current registration techniques, which may be invasive, expensive, inconvenient, slow, or inaccurate and may prevent certain types of approaches for certain surgeries such as posterior approach for brain surgeries. Additionally, the registration techniques described herein may provide a surgeon confidence that registration has occurred and that the registration is accurate. The surgeon, for example, may perform the registration moments before surgery to minimize drift because the process may be completed quickly.

Typically, calibration is a tedious and time-consuming process that requires precise instrumentation and expert involvement. By performing techniques described herein, the expense, time, and expert need may be reduced or eliminated. Particularly, when using the techniques described herein, a calibration may be done more often without needing to schedule an expert or obtain instrumentation. An increase in frequency of calibration allows for drift to be corrected in a robotic system daily, weekly, monthly, etc., which improves surgical outcomes. In some examples, a surgical procedure that is scheduled in advance may need to be canceled if an updated calibration is not performed. By using the calibration techniques described herein, the surgical procedure may be performed without canceling, as otherwise would be required.

In an example, tracking may be performed using systems and techniques described herein. For example, tracking of patient anatomy, a surgical instrument, or other objects within the surgical field may be tracked. Tracking may be used in robotic surgical techniques such that an object may be tracked within a surgical field and a location of the tracked object may be provided to a robotic surgical system. The robotic surgical system may use the tracked location of the object (e.g., patient anatomy), to perform a procedure (e.g., cut the anatomy at a particular location).

A robotic surgical technique using the systems and methods described herein may enable a posterior approach for a cranial procedure with a non-invasive and contactless method. The robotic surgical technique may be performed by a calibrated robotic system, use tracking, or be registered using systems and methods described herein.

Registration may include aligning real patient space (e.g., a coordinate system mapping an operating room or other surgical field) to a medical image space (e.g., a medical image, such as an x-ray, CT-scan, MRI, 3D image, video, etc.) into the surgical robot coordinate frame. The registration allows for a coordinate in the medical image space to be identifiable in the real patient space (or vice versa).

Some techniques for registration include point to point registration or point to surface registration. Point to point registration includes identifying anatomical landmarks or markers on a medical image or real patient and matching results. A navigation probe with attached markers may be used in identifying points. Point to surface registration includes obtaining a 3D surface model of patient anatomy and matching the 3D surface to a corresponding surface on a medical image. Again a navigation probe or a laser rangefinder attached to the end effector of a surgical robot (e.g. laser surface matching method of the ROSA robot) may be used to obtain points of the 3D surface on the patient anatomy. However, identification of anatomical landmarks may not be accurate or repeatable, may not be accurate enough for surgical uses, may be invasive, and may take a long time.

The systems and methods described herein avoid the above issues by registering real patient space and patient medical image space using a 3D camera (e.g., a structured light camera, a time of flight camera, two cameras, depth camera, etc.) and a laser range finder. The laser range finder may be attached or embedded onto an end effector of a robotic arm. The robotic arm and the laser range finder may be used to adequately place the 3D camera compared to the surface to be scanned and the measure range of the camera to obtain the best quality for the 3D acquisition. The robotic arm may be used to handle the 3D camera during acquisition and may provide orientation or position information related to the camera to perform a complete and accurate 3D reconstruction acquisition from different positions of the camera. The laser range finder may be used with the 3D camera to perform 3D surface acquisition at different patient positions (e.g., lateral, prone, etc.), which may be used to reach a specific pathology pathway (e.g., posterior approach to the skull).

The system and methods described herein include a 3D camera (e.g., a structured light (SL) camera, a time of flight (TOF) camera, etc.) integrating a laser range finder that may be coupled, attached, or embedded to an end effector of a robotic arm in order to perform one or more tasks associated with a robotic surgery. These tasks may include registration, verification of calibration, or tracking of patient anatomy movements.

Using a laser range finder with a 3D camera and a robotic arm allows for a fast, user friendly, intuitive, accurate, non-invasive and versatile method for 3D acquisition of patient anatomy. These systems and techniques provide visual verification of registration. The systems and techniques may be further used to perform posterior approaches for a cranial procedure in a non-invasive and contactless way. Without these systems and techniques, contact may be required due to a need for a rotational effect of the back of the head from a lack of number points of face matching. This rotational effect affects accuracy for posterior approaches. The systems and techniques provide a fast onsite verification method of the robot calibration.

FIG. 1 illustrates a robotic surgical system 100 in accordance with some embodiments. Robotics have become a useful tool for assisting the surgeon in the surgical field. A robotic device may assist in the surgical field performing tasks such as biopsies, electrode implantation for functional procedures (e.g., stimulation of the cerebral cortex, deep brain stimulation), open skull surgical procedures, endoscopic interventions, other "key-hole" procedures, arthroplasty procedures, such as total or partial knee replacement, hip replacement, shoulder implant procedures, or the like. In an example, a surgical procedure may use a surgical robot. The surgical robot may be tracked, such that a tracking system may determine a relative location of the surgical robot within a coordinate system or a surgical field. The surgical robot may have a different coordinate system or tracking system from a medical image (e.g., using known movements of the surgical robot to keep track of an end effector of a robotic arm of the surgical robot, which may include using sensors, such as a gyroscope, magnetoscope, accelerometer, etc.). In an example, a processor may be used to coordinate or translate information from the surgical robot coordinate or tracking system with a camera-based tracking system.

The robotic surgical system 100 may be used by the surgeon to perform a surgical procedure, such as on a knee joint of the patient. The robotic arm may use tracking information from a camera device, which may track anatomy of the patient (e.g., during surgeries such as for brain, spine, knee, hip, shoulder or any other anatomical part) or a surgical instrument, or another device, tool, or aspect of patient anatomy to perform the surgical procedure.

The robotic surgical system 100 may be used with the systems and methods described herein for 3D image, target, or other acquisition, such as for registration, calibration, or tracking. For example, as described below, the robotic surgical system 100 may include a camera affixed to an end effector of a robotic arm or embedded in a robotic arm, the camera used to register, calibrate, or track objects or coordinate systems for use during a surgical procedure, including, for example, registering a previously acquired patient image to a patient in a surgical field (e.g., by mapping the coordinate system of the patient image to a surgical coordinate system, such as that of the robotic surgical system 100).

The robotic surgical system 100 may include components, such as those described below with respect to FIGS. 2-4, including for example, a robotic arm, an end effector at a distal end (from a base of the robotic surgical system 100) of the robotic arm, a camera affixed to or embedded in the end effector, or a laser range finder, which may be affixed to or embedded in the camera or the end effector. Examples of these components are described in more detail below.

Figure 2:
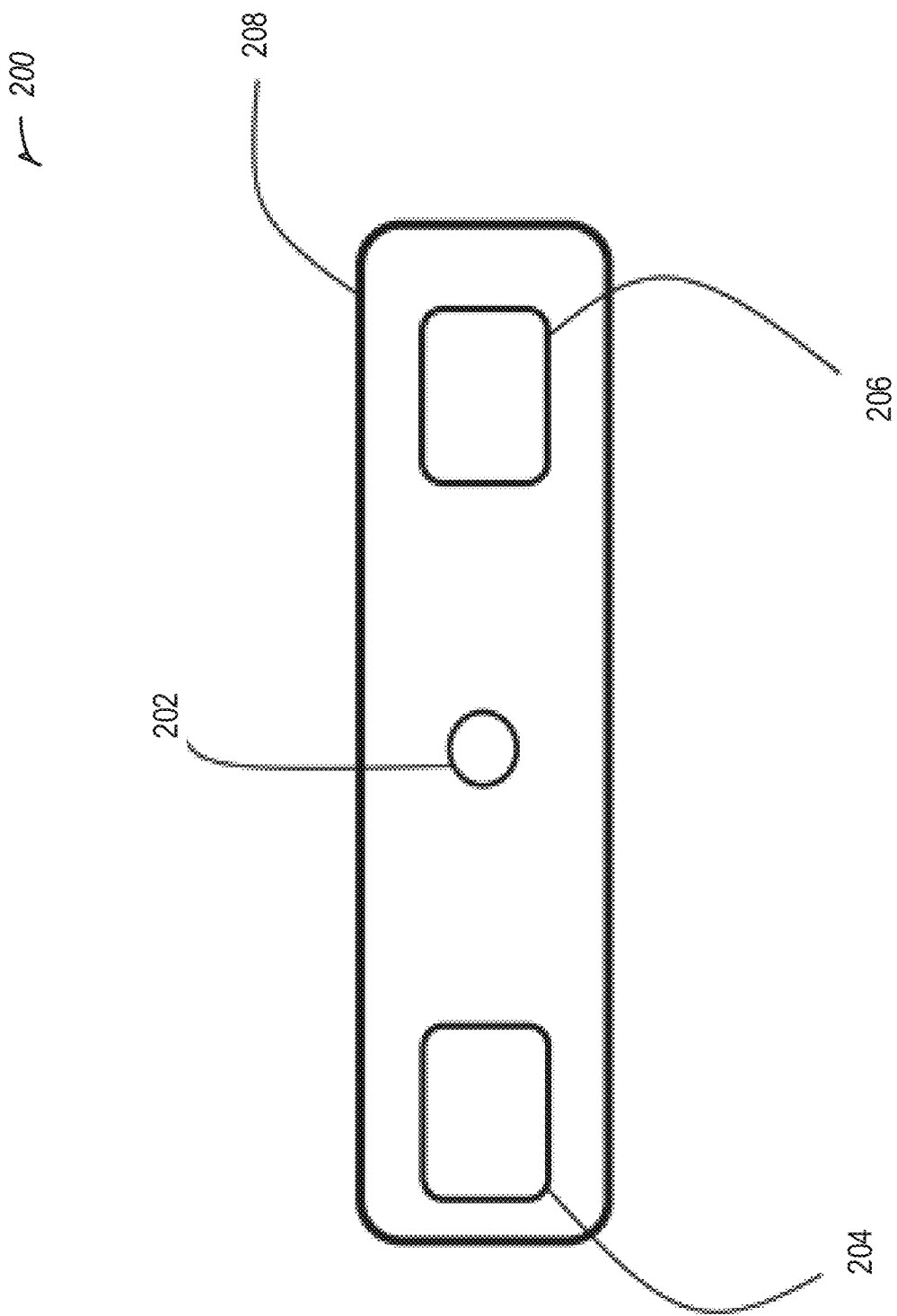
FIG. 2 illustrates a view of a camera for use in accordance with some embodiments.

FIG. 2 illustrates a view of a camera 200 for use in accordance with some embodiments. The camera 200 shown in FIG. 2 is an example camera that may be used with the systems and techniques described herein. Variations to the camera 200 that are not shown may be incorporated without deviating from the scope of the techniques described herein.

The camera 200 may include a laser emitter 202 (which may include a receiver, or may have a separate receiver component 206, such as a light and laser receiver), a structured light projector 204, and may be enclosed by a case 208. In another example, the camera 200 may be any camera capable of capturing depth information, such as a depth camera, a time of flight camera, a 3D camera, two cameras, a structured light camera, light-field camera, plenoptic camera, or the like. The laser emitter 202 may be embedded in the camera 200 or may be affixed to the camera 200. The laser emitter 202 may include a laser rangefinder configured to identify distance information of an object when laser light is emitted towards the object and reflected back from the object. A receiver of the laser light may be part of the laser emitter 202, or separate, and may be embedded in the camera 200 or affixed to the camera 200. The structured light projector 204 may project structured light, which when reflected off a surface or surfaces and received at the receiver component 206 may be used to determine depth of the surface or surfaces.

The camera 200 and laser rangefinder may be used in a cooperative mode with a robotic surgical system (e.g., that described in FIG. 1) and a surgeon (or other operator). In an example, a handle may be affixed to or be included as part of the case 208 of the camera 200. The cooperative mode allows a surgeon or other operator to generally move the camera or laser rangefinder (e.g., under power of a robotic arm of the robotic surgical system) to a position such that the camera or laser rangefinder may capture distance information to a particular object.

The camera and laser rangefinder technique may be used to identify, register, calibrate, or track distance, position, or location information for various objects, such as an object during a surgical procedure. For a brain surgery, a face of a patient may be what is scanned, and the surgeon or other operator may place the camera 200 above the patient. The camera 200 or laser rangefinder may then be used to map features of the patient's face.

In an example, the camera 200 or the laser rangefinder may have an effective range or have improved function over a particular range. For example, the laser rangefinder may be used to adjust the camera 200 and the object (e.g., the face of the patient) to place the camera 200 within the ideal range or at a best distance.

The laser rangefinder may output distance information, which may be used to trigger an alert or output information, such as on a user interface. For example, in an example when the camera 200 is within a particular range or at a particular distance based on information captured by the laser rangefinder, an LED may be illuminated to identify to a user that the camera 200 is correctly placed. In another example, the distance information captured by the laser rangefinder may be used by the robotic surgical system to iteratively move the robotic arm with the camera 200 and identify a new distance with the laser rangefinder or based on an image captured by the camera 200, until the camera 200 is at a particular distance or within a particular range of distances from an object.

In an example, the camera 200 may include a trigger to launch acquisition of distance information. The camera 200, in one example, may automatically register real space to a medical image in response to the trigger (e.g., with no further human involvement). In another example, a user may use the robotic arm in a cooperative mode to move the camera 200 to an initial location. In this example, the iterative process may automatically take over once the camera 200 is within a particular distance of an identifiable object (e.g., based on images captured by the camera 200, such as when a face is detected as being present within an image) or based on a trigger.

The camera 200 or laser rangefinder may output information to a user interface, such as images captured by the camera 200 or distance information identified from received data via the laser rangefinder or the camera 200. In an example, the distance information may be used to display registration data in real-time. The camera 200 may register real space points to a medical image, such as in real-time. In an example, verification of the real space points may include using traditional registration (e.g., a probe or handle). In an example, 2,000 to 40,000 points may be captured for registration.

The tracking data imaged by a camera device or collected by an image processing system (e.g., using a processor) may be used to determine a position and an orientation of a tracked object within a virtual three-dimensional coordinate system (e.g., within the surgical field). The tracking data may include the position and direction of the camera device. The image processing system may output the position and the orientation of the tracked object. The output data may include coordinates in a virtual three-dimensional coordinate system. The output may include one or more of the captured synchronized images that includes the tracked object.

Figure 3:
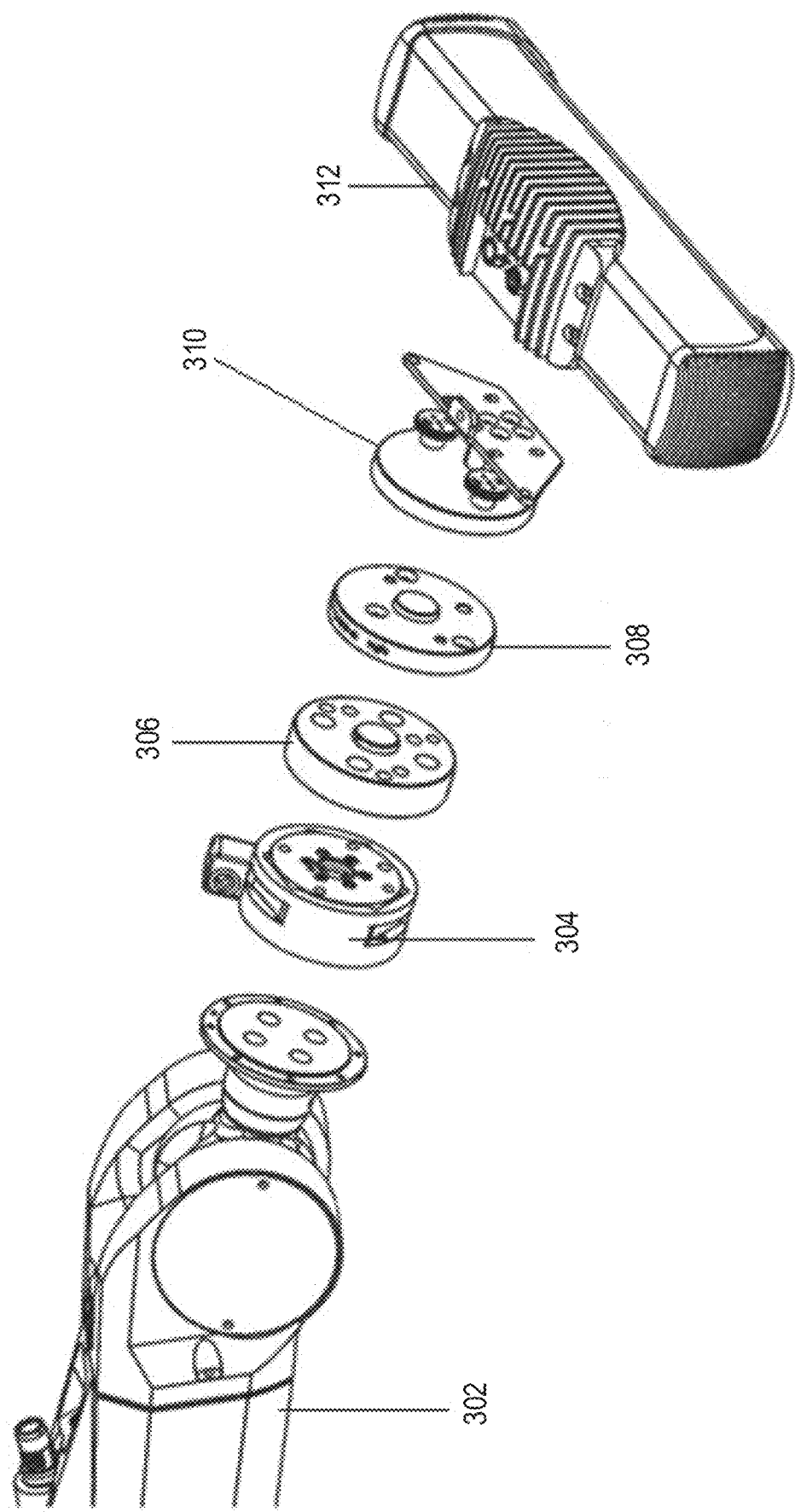
FIG. 3 illustrates an end effector assembly for use with a robotic surgical system in accordance with some embodiments.

FIG. 3 illustrates an end effector assembly 300 for use with a robotic surgical system in accordance with some embodiments. The end effector assembly 300 may be coupled to a robotic arm 302 of a robotic surgical system (e.g., 100 of FIG. 1). The end effector assembly 300 may include components, such as a force sensor 304, an insulation component 306, a sterile interface 308, or a camera 312 to robot interface component. In an example, the camera 312 may be embedded in an end effector. In another example, the camera 312 may be affixed to the end effector (e.g., via the camera 312 to a camera to robotic interface component 310). In either example, the camera 312 may be independently powered or draw power via the robotic arm 302. Similarly, in either example, the camera 312 may have an independent data connection (e.g., via wireless communication) or may connect to a processor or memory via a data connection of the robotic arm 302. The various components of the end effector assembly 300 may be connected in different orders, although some components may have relative location rules (e.g., the sterile interface 308 may be required to be located between sterile and non-sterile components). The end effector assembly 300 may include a component to receive a tool, such as a cut guide, a cutting device, or other surgical tool to perform a surgical procedure. The tool may be attached to the end effector assembly 300, such as in a configuration where the camera 300 is embedded in an end effector component.

Figure 4:
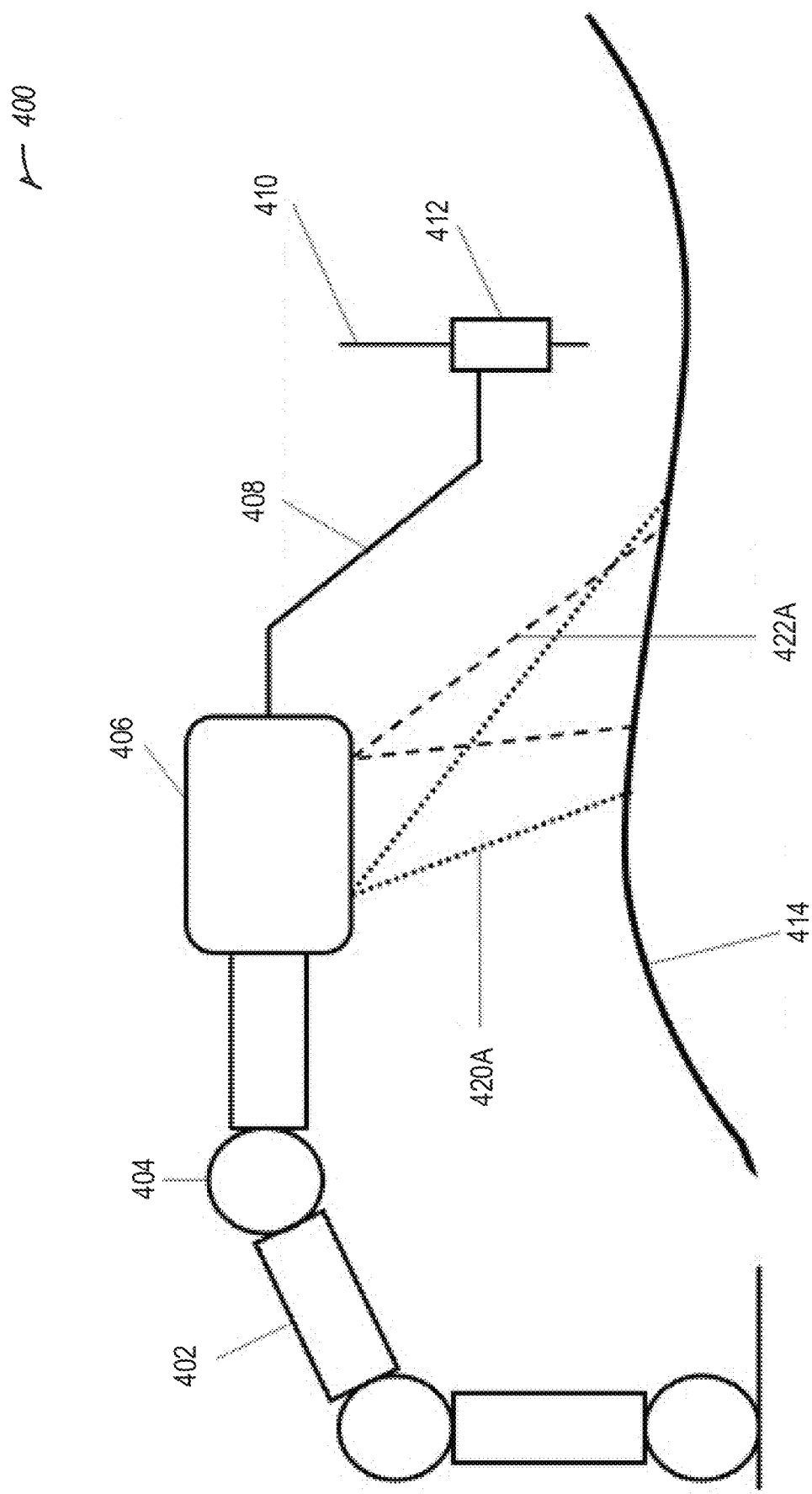
FIG. 4 illustrates a camera configuration for use with tracking in accordance with some embodiments.

FIG. 4 illustrates a camera configuration for use with tracking in accordance with some embodiments. The camera configuration illustrated in FIG. 4 is part of a surgical field 400, which includes a robotic arm and a patient (including specific patient anatomy 414). The robotic arm may include one or more segments (e.g., 402) connected by joints (e.g., 404), an end effector 406 (such as described in FIG. 3, which may include a force sensor, camera, insulation, or a sterile interface), or a robot to tool guide interface 408 connecting a tool 410, such as a surgical tool or a tool guide 412.

The camera of the end effector 406 may be used to capture an image of the patient anatomy 414. In an example, the camera projects structured light and captures an image based on a field of view 420A (which may differ from a projected light field of view 422A, which may be projected by a structured light projector of the end effector 406) on the patient anatomy 414. The robotic arm may move the end effector 406 to change the field of view of the projector 422A or the camera sensor 420A (used to capture an image).

When the patient anatomy 414 moves, the camera may capture a surface of the patient anatomy 414, which may be used to identify movement of the patient anatomy 414. In an example for tracking the patient anatomy 414, the robotic arm may move with the patient anatomy 414 (e.g., as identified by the captured image from the camera). For example, as the patient anatomy moves, the robotic arm moves, such that the tool 410 or tool guide 412 or aspect of the end effector 406 may remain stationary relative to the patient anatomy, though the tool 410 or tool guide 412 or aspect of the end effector 406 moves with the robotic arm in absolute space. In this example, the robotic arm is configured to follow the patient movement automatically.

The robotic arm and end effector 406 with optional components such as the camera (and optionally a tool 410 or tool guide 412) may be used to register the patient anatomy 414 to a medical image, calibrate the robotic arm orientation or movement, or track the patient anatomy 414 in real time. Various techniques for registration, calibration, or tracking are described below. The robotic surgical arm shown in the surgical field 400 is referenced as an example, although other components, combinations, or types of robotic arms and devices may be used.

In an example, the robotic arm may be placed in a cooperative mode where a surgeon or other operator moves the camera via the robotic arm. The camera may include a laser rangefinder to accurately and quickly identify distance of the camera to an object, such as patient anatomy. For registering patient anatomy to a medical image, the cooperative mode and the laser rangefinder may be used with the following technique.

This technique includes activating the robotic arm and placing it in the cooperative mode, with a camera on or in the end effector 406 of the robotic arm. The camera may be moved by using the robotic arm in the cooperative mode (e.g., via a handle on the camera or the end effector 406). The camera may be placed above the surface to be scanned.

Once the camera is placed above the surface to be scanned the user may use the cooperative mode to manually adjust the camera position in order to be within the best Measure Range (MR) of the surface by using the laser rangefinder incorporated in or on the camera. In an example, an indicator light (e.g., an LED) may be used to indicate when the MR is within a specified range for acquisition of images by the camera. The range may be determined by using the distance information between the laser rangefinder and the surface.

In another example, once the camera is placed above the surface to be scanned, the user may activate an automatic mode to let the system automatically adjust the camera position (e.g., by autonomously moving the robotic arm) in order to be within the best Measure Range (MR) by using the distance data provided by the laser rangefinder incorporated in or on the camera.

After the camera is correctly placed (e.g., is within the MR) above the surface to be scanned, a 3D acquisition technique may be initiated to capture images of the surface using the camera (in an example, a triggering device, such as a button may be configured directly on the camera or on a case or handle of the camera, in other examples, the process may be initiated by selecting an appropriate indicator on a user interface).

Using the acquired images, automatic registration between a 3D model (e.g., generated from the acquired images) and 3D data (e.g., from medical images) may be performed. Visual verification of the registration using the laser rangefinder or a light projector (when using a structured light camera) may be performed by pointing the laser rangefinder or light projector at an anatomical landmark and visually checking whether the registration is accurate. When the registration is verified, the process may be completed and the camera may be removed from the robotic arm, such as to be replaced by an instrument for performing a surgical procedure. When the registration is not verified, the registration may be repeated, such as with additional positions for acquiring images to increase accuracy.

In another example technique, the cooperative mode may be used with a 3D camera without using a laser rangefinder. In this example, image processing is used to find features (e.g., of patient anatomy, such as a face or head), rather than using the laser rangefinder to find distance. The 3D camera may be used to identify each feature, with the camera moved until different features are identified.

This technique includes moving the camera using the robotic arm in the cooperative mode. The camera may be placed above the surface to be scanned. When the robotic arm or camera is in position, a 3D acquisition technique may be launched and checked (e.g., automatically with the aid of AI techniques or manually by using the visual of the 3D acquisition on a display). When an image captured by the camera identifies a part of the head of the patient, for example, the image or position may be verified. Depending on the part identified in the images captured by the camera or when the camera does not provide any identifiable features, the user may to adjust the robotic arm or camera position by using the cooperative mode.

When the robotic arm is in the new position, the 3D acquisition may be relaunched and checked again using the visual of the 3D acquisition on a display. When the visual is not verified, the user may adjust the robotic arm position by using the cooperative mode. These operations may be iterated until the visual is verified.

Once the camera is correctly placed above the surface to be scanned (e.g., verified), the 3D acquisition by the camera may be initiated. Automatic registration between a 3D model (e.g., based on the captured images) and 3D data from medical images may occur using a registration technique (described in more detail below) Visual verification of registration may be performed by a user via the laser rangefinder or the light projector in case of a structured light camera by pointing the laser or light at an anatomical landmark and visually checking whether the registration is correct.

When the registration is verified, this technique may be completed with the camera removed from the robotic arm and, for example, replaced by an instrument to perform a surgical procedure. When the registration is not verified, the registration process may be repeated with additional camera positions for acquisition to increase the accuracy.

In another example technique, an automatic mode may be used with a 3D camera with or without using a laser rangefinder or user interaction. In this example technique, the automatic mode may register real space to medical image space without user involvement beyond initiating the process.

For example, the robotic arm may automatically move to a correct location for the camera to capture images of a surface or patient anatomy. As the patient anatomy (e.g., the head) is attached to the robot during the surgical procedure, the coordinate system of the robot may be mapped to approximatively where is the anatomy is located in real space. Using that information, the robotic arm may move automatically until the camera is placed approximatively above the patient anatomy.

In an example using the laser rangefinder, when the robotic arm is in position, the automatic mode may be activated, and using a laser rangefinder, the robotic arm may automatically adjust the camera position in order to be within the best Measure Range (MR). For example, the robotic arm may move according to distance data provided by the laser rangefinder incorporated in or on the 3D camera.

When the camera is correctly placed above the surface to be scanned, the 3D acquisition may be launched automatically. Automatic registration between a 3D model (e.g., generated from captured images) and 3D data from medical images may be performed.

In an example not using the laser rangefinder, when the robotic arm is in position, the automatic mode may be activated, and using images captured from the camera, features of the patient anatomy may be identified. When features are not identifiable, the robotic arm may move the camera and the attempt to identify the patient anatomy may be repeated. When a feature is identifiable, the feature may be identified, and based on the identified feature, it may be determined whether the camera is in range or position for registration. When the camera is not in position or range, the robotic arm may move based on the identified feature to within range or in a specified position.

In an example, visual verification of the registration using the laser rangefinder or the light projector in case of a structured light camera may be performed by pointing the laser or light at an anatomical landmark and visually checking whether the registration is accurate. When verification is accurate, then the registration process is finished, and the camera is removed from the robotic arm and optionally replaced by an instrument. When verification is not accurate, the registration may be redone with additional positions for acquisition to increase the accuracy. In an example, the visual verification may be skipped for a completely automated process.

The above techniques describe registration of real space to medical data (e.g., previously acquired medical images). Other uses of the camera configuration shown in the surgical field 400 include calibration of the camera or robotic surgical system or tracking objects within the surgical field 400, each of which is described in turn below.

When the robotic surgical device is initially set up, it is calibrated to the surgical field 400, including for example, calibration of coordinate system for use when the robotic arm is moved or moves. Calibration may also be used when, over time and due to use, drift occurs (e.g., due to vibration caused by some mechanical parts). Without the techniques described herein, a costly and time-consuming process including a site visit by an engineer may be required.

The techniques described herein allow for a fast and accurate calibration, which may be performed monthly, weekly, daily, or before each surgical procedure. The calibration described herein may eliminate or drastically reduce drift errors. The camera shown in the surgical field 400 may be used pre-operatively for calibration, or intra-operatively for registration or tracking.

During calibration, a reference object (not shown in FIG. 4) may be used. The reference object may be affixed to a base of the robotic surgical device, or otherwise placed in a location of known distance and orientation to the camera embedded or affixed to the end effector of the robotic arm. The reference object has a known geometry (e.g., a pyramid, a cube, etc., optionally with different colors, such as dark and light, or distinguishable shapes, such as spheres like an optical tracker).

In an example, a calibration technique may include moving the robotic arm along a trajectory, which may be predefined, random, or controlled cooperatively. Based on images captured by the camera during the movement along the trajectory, the relative location of the reference object to the camera may be determined. This determination may be based on the known location of the reference object, as well as the orientation and geometry of the reference object. The robotic arm may be automatically calibrated by comparing the reference object to stored imaging. For example, a 3D model of the reference object may be generated, and from the trajectory of the camera, identifiable features or points of the reference object that should be visible to camera may be determined. These identifiable features or points may be compared to locations in the image of the 3D model from that trajectory. When the features or points are not correctly aligned, the robotic arm may require a recalibration. When the features or points are correctly aligned to the expected results, the calibration is complete, and the robotic arm may be determined to be accurately calibrated. Recalibration may include running a program that adjusts the origin, distances, etc. of the robotic arm to regenerate a coordinate system based on the current status of the robotic arm. In an example, the calibration test takes 5-6 minutes (or less), and may be performed before a surgical procedure. In an example, at least 10 different preregistered positions or configurations of the robotic arm may be used to calibrate the robotic arm to the reference object.

Tracking objects in the surgical field 400 is difficult due to the speed and accuracy required. Some techniques rely on optical reference markers that are tracked by a camera. These reference markers may be invasive (e.g., affixed to a bone of the patient) or may require line of sight to the particular reference marker. The tracking techniques described herein may be used without a reference marker or may use multiple features or points (e.g., these techniques may not need to track any specific feature or point, but instead may track any identifiable feature or point that is in a line of sight). Tracking techniques may be used to track tools, instruments, aspects of a robotic arm or end effector, or patient anatomy.

In an example, tracking patient anatomy as it moves using the camera includes using the camera to provide snapshots of the surface to be tracked at least at a specific frequency. The frequency may be adapted to the movement speed of the patient anatomy (for example, at least 60 Hz). The camera may be a structured light camera. In an example, because visible light is used (e.g., not x-ray), only visible surfaces may be acquired in images captured by the camera. This tracking technique may be used with "open" surgical procedures, such that the camera may capture the bone or patient anatomy to be tracked. In another example, this tracking technique may be used with some types of minimally invasive surgery (MIS), such as for spine, as the movement of the skin above the spine provides sufficient information about the movement of vertebras as muscles and ligaments are linked to skin and vertebras. By using a soft tissue deformation model, bone movement may be calculated based on skin movement for bones where skin is close to bone and linked by muscles and ligaments. The robotic arm may be moved relative to bone movement based on skin movement information acquired by the camera.

The tracking technique may include launching a tracking mode via the robotic arm, such as in response to a button press on the robotic arm or the camera, a voice command, an interaction with a user interface, a foot pedal, using force sensor information of the robotic arm, or the like. The camera may acquire a first snapshot of the surface (e.g., an image) and store it to memory. The camera may acquire a second snapshot after a certain time (e.g., with a frequency that is adapted to the motion speed of the patient anatomy 414) and store it to memory. A processor may be used to compare the two snapshots and determine whether there is a change in location of the patient anatomy 414 from the first to the second image. When there is no change, the robotic arm may stay in place and the camera may acquire a new snapshot after a specified time (according to the frequency). The processor may compare the new snapshot to the first or second image and determine whether there is a change. This process may be iterated.

When there is a change from the first image to the second image in the position of the patient anatomy 414, the robotic arm may move according to determined patient anatomy motion (e.g., the robotic arm may track the patient anatomy by following movements of the patient anatomy). After the robotic arm has moved, the camera may acquire a new snapshot to have a new reference of the patient anatomy 414. The camera acquires a second new snapshot at the new location after a certain time (frequency) and stores it to memory. The processor compares the two new snapshots to determine whether there is a change in location of the patient anatomy 414. This process may be repeated and iterated as the patient anatomy 414 moves or remains stationary during the surgical procedure.

The tracking may be used for when the robotic arm is performing or aiding in a portion of a surgical procedure. For example, the end effector 406 may include a cut guide aligned to the patient anatomy 414. The patent anatomy 414 may be tracked, and the robotic arm may move such that the cut guide remains aligned to the patient anatomy 414 (e.g., the cut guide does not move relative to the patient anatomy 414, though the cut guide moves relative to the surgical field 400). In another example, a surgical tool may be coupled to the end effector 406 for performing a cut, a burr, inserting a device, or the like. The surgical tool may similarly track the patient anatomy, but may move relative to the patient anatomy as needed for the surgical procedure. Put another way, the surgical tool and the patient anatomy 414 may remain in the same inertial reference frame relative to each other, though both may move relative to the surgical field 400, and the surgical tool may move relative to the patient anatomy 414 within the inertial reference frame when needed for the surgical procedure.

Figure 5:
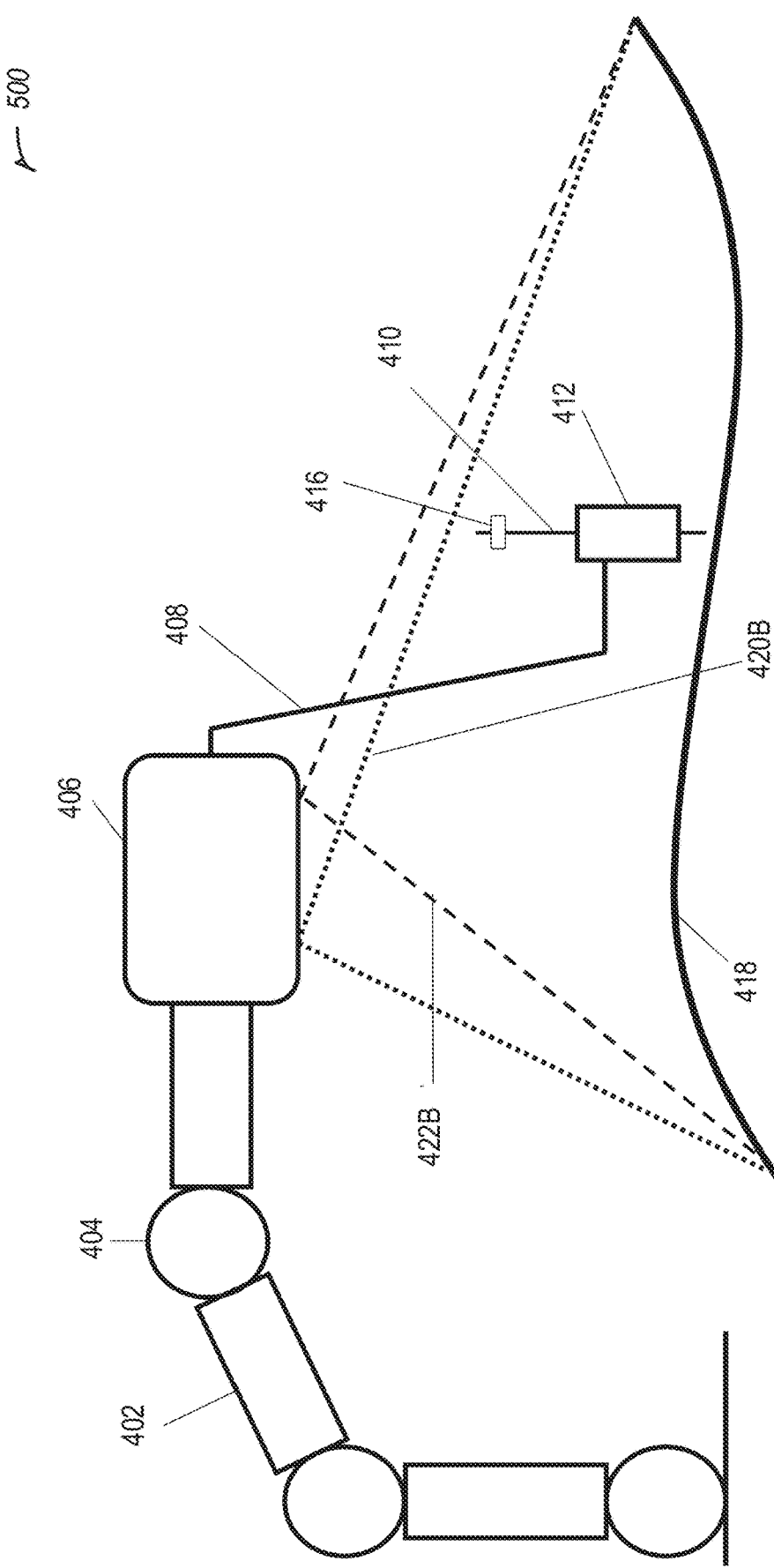
FIG. 5 illustrates a system for tracking an instrument inserted into an instrument guide held by a robotic arm in accordance with some embodiments.

FIG. 5 illustrates a system 500 for tracking an instrument inserted into an instrument guide held by a robotic arm in accordance with some embodiments. The system 500 includes a camera configuration and robotic arm similar to FIG. 4 described above. A patient, including specific patient anatomy 418 is also illustrated in FIG. 5. The robotic arm of system 500 may include one or more segments connected by joints, the end effector 406 (such as described in FIG. 3, which may include a force sensor, camera, insulation, or a sterile interface), or a robot to tool guide interface 408 connecting a tool 410, such as a surgical tool or a tool guide 412. The robotic arm of system 500 is illustrated with a tool reference 416 attached to the tool 410 or embedded in the tool 410. The tool reference 416 allows the tool 410 to be tracked via the camera.

When the tool reference 416 is moved, the camera may capture an image of the tool reference 416, which may be used to identify movement of the tool reference 416. Tracking the tool 410 may be used to maintain safety distances from the patient, to perform automated or force-assisted surgical techniques, to align the tool 410, or the like. In an example, when tracking the patient anatomy 418, the robotic arm may move the tool (based on also tracking the tool via the tool reference) with the patient anatomy 418 (e.g., as identified by the captured image from the camera). For example, as the patient anatomy 418 moves, the robotic arm moves, such that the tool 410 or tool guide 412 or other aspect of the end effector 406 may remain stationary relative to the patient anatomy 418, though the tool 410 or tool guide 412 or other aspect of the end effector 406 moves with the robotic arm in absolute space. In this example, the robotic arm is configured to follow the patient movement automatically.

The robotic arm and the tool reference, with optional components such as the camera (and optionally a tool or tool guide), may be used to register patient anatomy to a medical image, calibrate the robotic arm orientation or movement, or track patient anatomy in real time. Various techniques for registration, calibration, or tracking are described above with respect to FIG. 4.

The system 500 illustrates the patient anatomy 418 and the robotic arm in a different orientation than in FIG. 4. In FIG. 5, a projector field of view 422B is different based on the changed configuration, as is a camera field of view 420B. The fields of view may be adjusted by moving the robotic arm.

Figure 6:
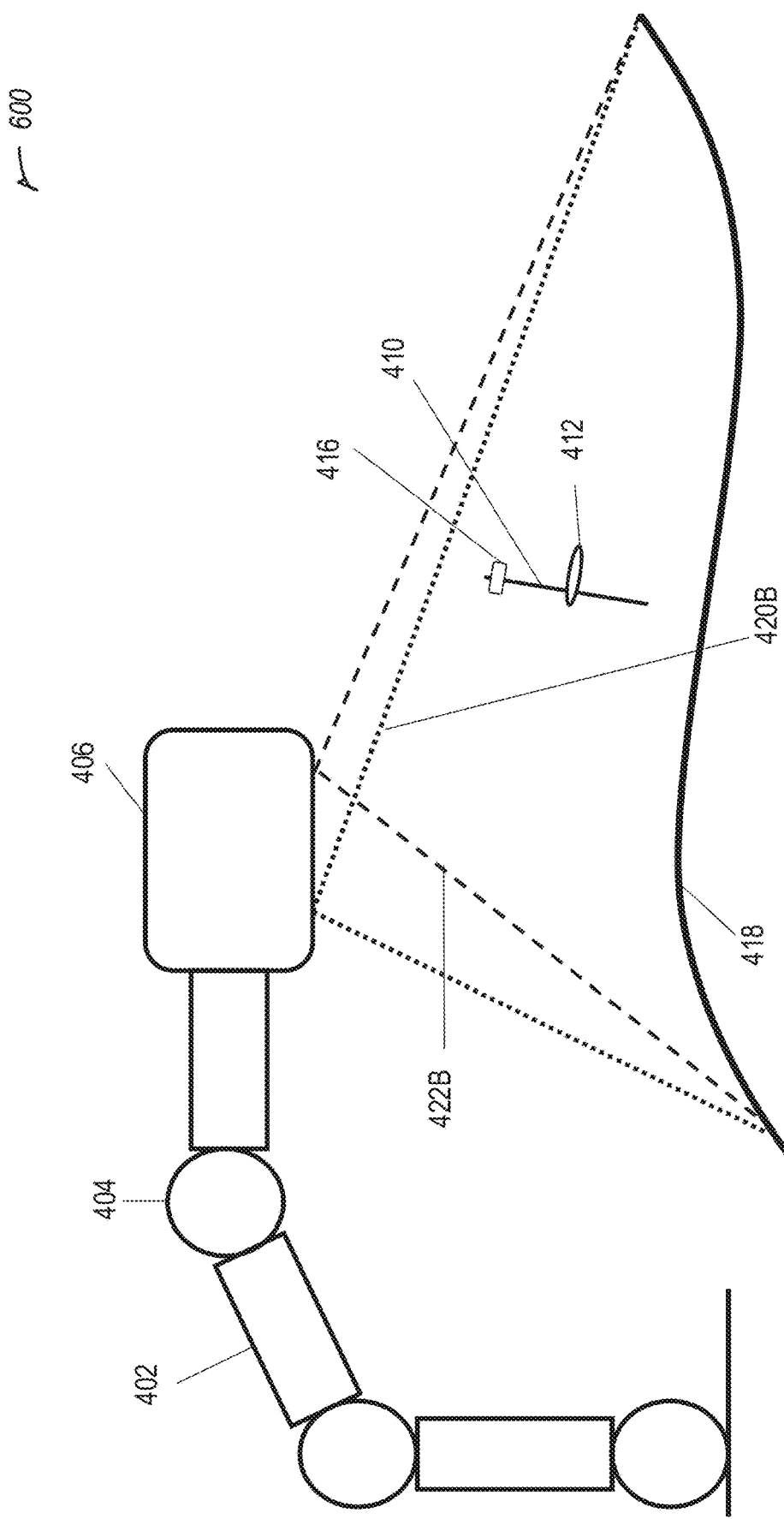
FIG. 6 illustrates a system for tracking an instrument handheld by a surgeon in accordance with some embodiments.

FIG. 6 illustrates a system 600 for tracking an instrument handheld by a surgeon in accordance with some embodiments. Similar techniques as described above for FIGS. 4-5 may be used for tracking the tool 410 via the tool reference 416 in the setup of system 600. In system 600, rather than the tool 410 being attached to the robotic arm, the tool 410 is handheld (e.g., by a surgeon's hand 412). The camera may be used to track the tool 410 via the tool reference 416 as well as or instead of the patient anatomy 418. When both the tool 410 and the patient anatomy 418 are tracked, information may be displayed on a user interface to provide tracking information, for example based on a registered image.

Figure 7:
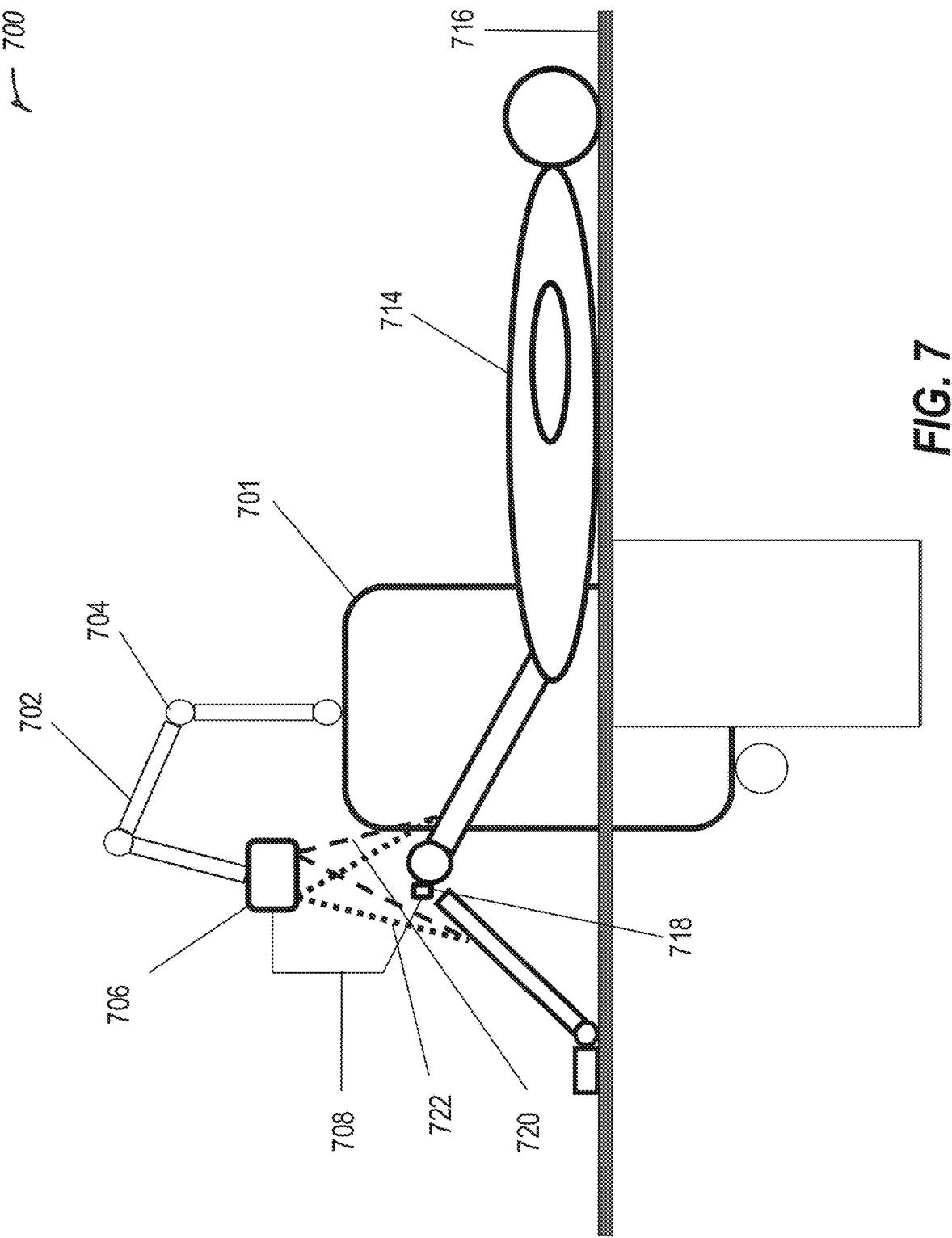
FIG. 7 illustrates a system for bone tracking during a knee procedure in accordance with some embodiments.

FIG. 7 illustrates a robotic surgical system 700 for bone tracking during a knee procedure in accordance with some embodiments. System 700 includes a specific implementation of the techniques described herein including knee surgeries, such as a knee arthroplasty, ligament repair, etc. FIG. 7 illustrates a robotic surgical system 700 with a robotic arm segment 702, a joint 704, and the robotic stand 701, for example sitting on a surgical table 716. A tool guide 718 may be used with the robotic surgical system 700.

In an example, FIG. 7 illustrates the use of a Structured Light camera (SL cam) attached or embedded into an end effector 706 (e.g., which may be the same or have a different configuration or components as end effector 406 of FIGS. 4-6) of the robotic arm for a knee surgery. At the beginning of a procedure, such as when the knee surgery is an open one, the robot may register the patient anatomy 714 (e.g., femur, tibia, etc.) for example by matching a 3D data from the SL cam (in an example, a single snap shot may be sufficient) with a generic 3D model or a 3D model based on preoperative medical images of the patient bones. When patient anatomy 714 is registered, the SL cam may then be used in order to track knee bones (e.g., femur and tibia) movements, such as by using the techniques described herein. The tracking of the bones may allow the robotic arm to move such that the cut guide attached to the end effector 706 (e.g., via a specific robot/tool guide interface piece 708) remains aligned to the patient anatomy 714 (e.g., the cut guide does not move relative to the patient anatomy, though the cut guide moves relative to the surgical field). This non-invasive tracking technique avoids the need of pinning bones movement optical tracking references into bones. The SL cam may project a field of view 722 and have a sensor field of view 720.

Figure 8:
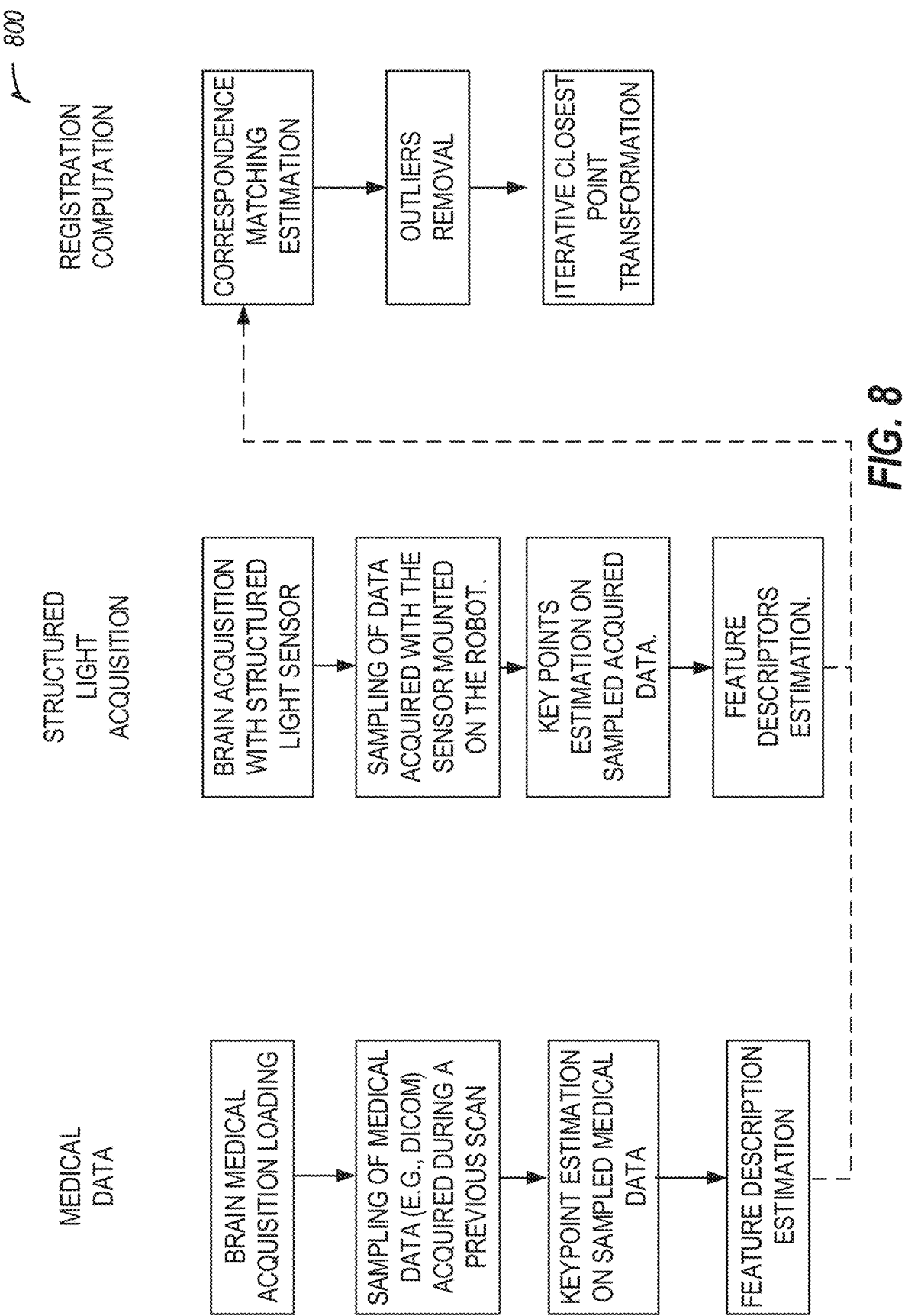
FIG. 8 illustrates a flowchart showing an automatic registration technique in accordance with some embodiments.

FIG. 8 illustrates a flowchart 800 showing an automatic registration technique in accordance with some embodiments. The flowchart 800 includes registration preprocessing and registration computation. In an example, portions of the preprocessing may be performed separately, such as at a different time or by a different component. For example, the medical data preprocessing may be performed after imaging a patient, pre-operatively, while the structured light acquisition preprocessing may be performed intra-operatively.

The registration preprocessing includes preparing a coordinate system or location information for a medical image (e.g., a 3D medical image, such as a CT-scan or an MRI, or may include multiple medical images) and preparing a coordinate system or location information for a robotic surgical device. The registration computation describes a process of relating the coordinate system or location information of the medical image to that of the robotic surgical device.

Preprocessing is performed on medical data by acquiring medical data (e.g., a brain image), sampling the medical data (e.g., selecting a plurality of points of a point cloud), estimating keypoints on the sampled data, and estimating feature descriptors for the keypoints. A similar preprocessing is performed on data acquired via a structured light camera (or other depth or 3D camera), including sampling, keypoint estimation, and feature descriptor estimation. The sampling may include uniform sampling on the medical data point cloud and the structured light image point cloud. Retaining uniform sampling may improve precision when registering the medical data to the structured light data. The keypoint estimation for the medical data and the structured light data may include generating new respective point clouds which may include a reduced panel of discriminative points with characteristics relevant to registration, for example. The feature descriptors may be used to establish matched pairs of points between the medical data point cloud and the structured light image point cloud.

After preprocessing, the flowchart 800 includes computation for registering the medical data to the structured light data. Corresponding points between the medical data point cloud and the structured light image point cloud may be estimated. In an example, correspondences of points with unverified criteria may be rejected. The criteria may include distance between the points (e.g., Euclidean distance). Distance may be measured relative to local coordinate systems of the medical data or the structured light data, or to other features of the data. Outliers may be removed, in an example. The final correspondence determination may include an iterative closest point transformation. The flowchart 800 includes performing the iterative closest point transformation by iteratively computing transformation (e.g., including rotation and translation) between the two point clouds to minimize total distance, for example. The minimization may include using a root mean square and reaching convergence when the root mean square falls below a threshold. The minimized point cloud to point cloud correspondence may be output as a transformation (e.g., rotation or translation of one or both of the point clouds), which may be used to map a coordinate from a medical image to a coordinate in real space (e.g., as captured by the structured light camera). After mapping, a real space coordinate, point, feature, or object may be identified as corresponding to a coordinate, point, feature, or object of a medical image, for example in real time.

Figure 9:
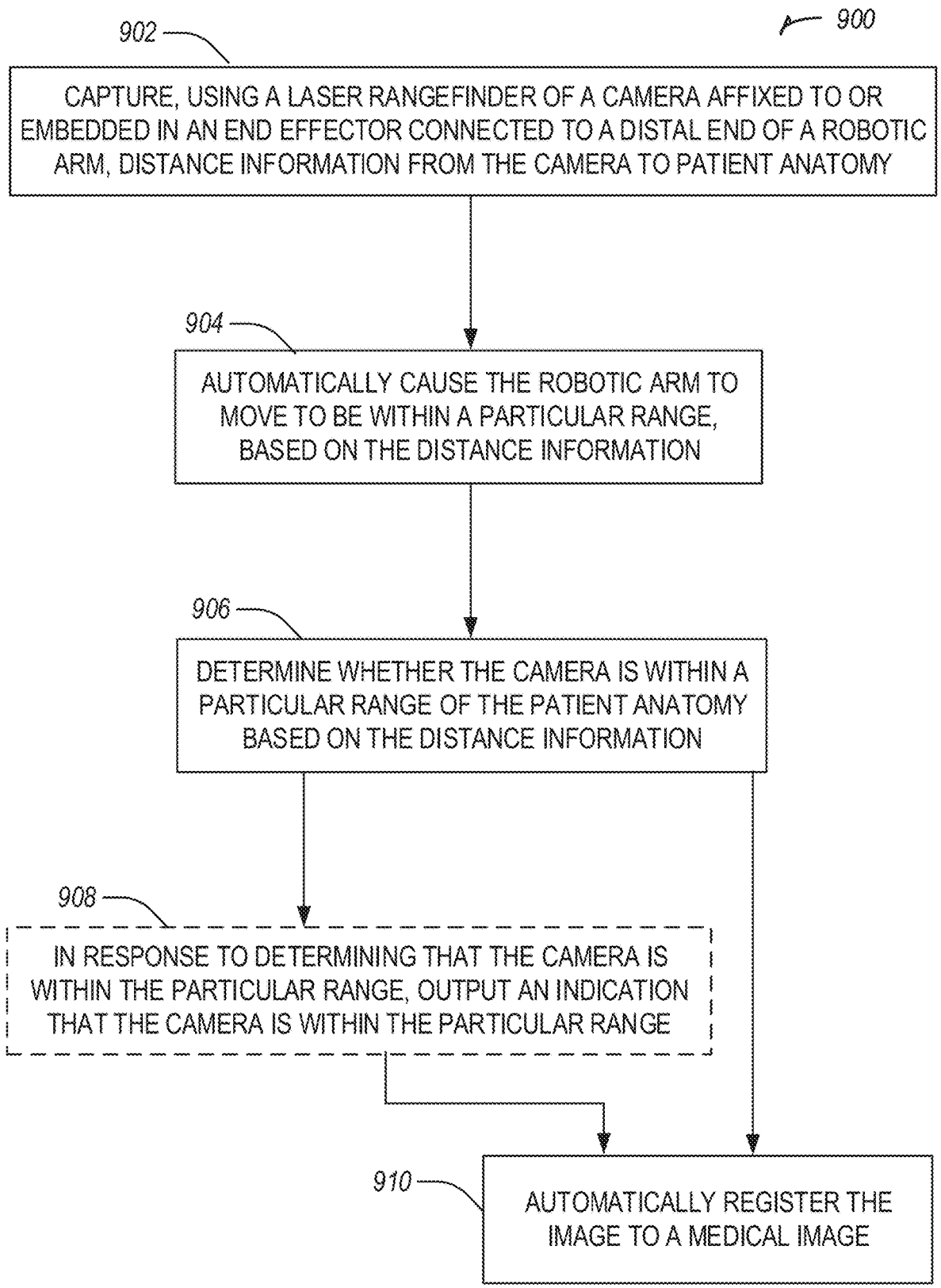
FIG. 9 illustrates a flowchart showing a technique for registering patient anatomy during a surgical procedure or calibrating a robotic surgical device in accordance with some embodiments.

FIG. 9 illustrates a flowchart illustrating a technique 900 for registering patient anatomy during a surgical procedure or calibrating a robotic surgical device in accordance with some embodiments. In an example, operations of the technique 900 may be performed by a processor, executing instructions stored in memory.

The technique 900 includes an operation 902 to capture, using a laser rangefinder of a camera affixed to or embedded in an end effector connected to a distal end of a robotic arm, distance information from the camera to patient anatomy. In another example, operation 902 may use images captured by the camera rather than the laser rangefinder to determine distance information or to determine whether a captured image includes a particular portion (e.g., a feature) of patient anatomy.

The technique 900 includes an operation 904 to automatically cause the robotic arm to move to be within a particular range, based on the distance information.

The technique 900 includes an operation 906 to determine whether the camera is within a particular range of the patient anatomy based on the distance information.

The technique 900 may include an operation 908 to, in response to determining that the camera is within the particular range, output an indication that the camera is within the particular range. When the camera is outside the particular range, the robotic arm may be moved cooperatively with a user or automatically to a new location, and the technique 900 may be iterated to determine whether the camera is within the particular range.

The technique 900 includes an operation 910 to automatically register the image to a medical image. In an example, the camera may be used to track the patient anatomy after registration.

Figure 10:
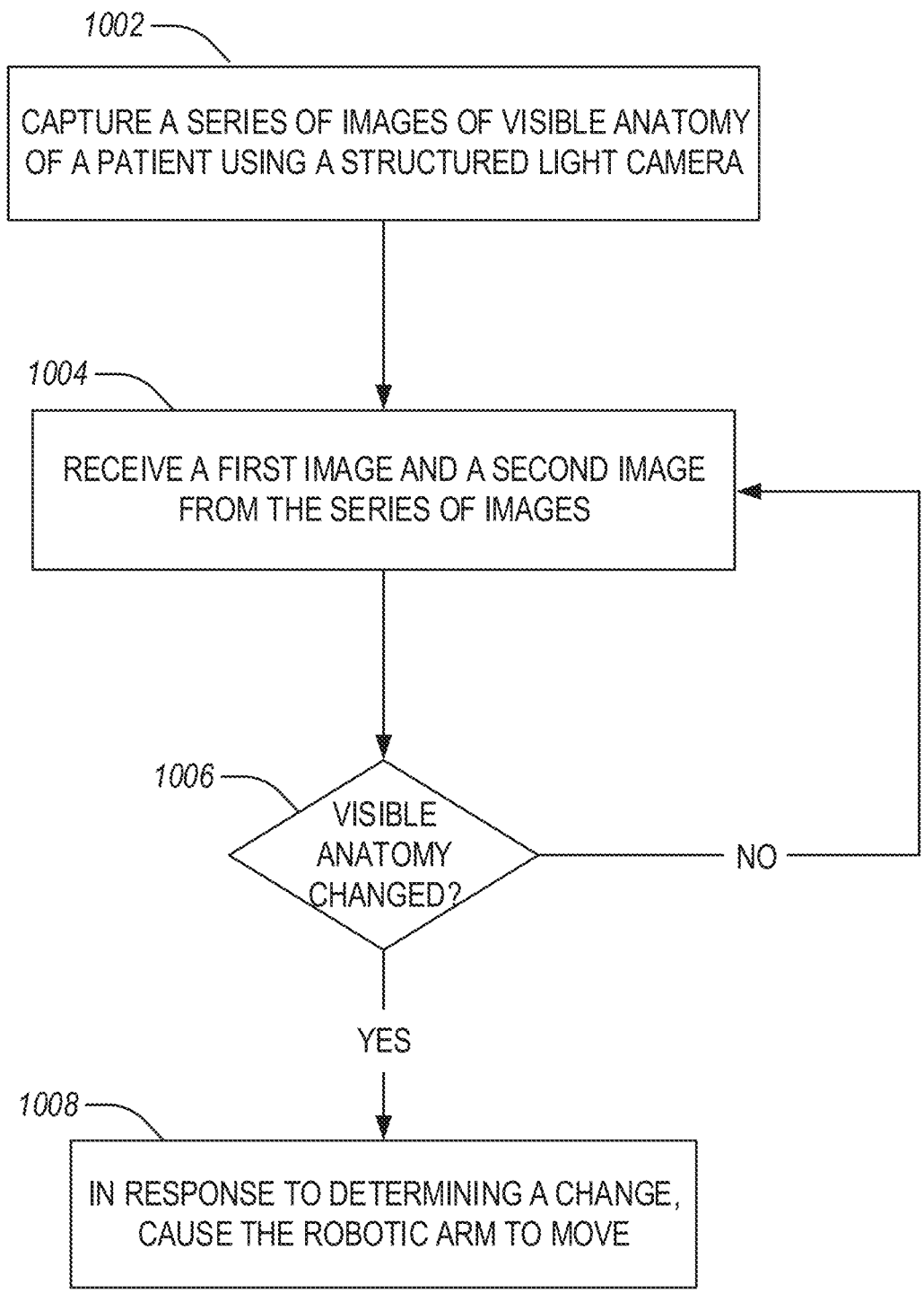
FIG. 10 illustrates a flowchart showing a technique for tracking patient anatomy during a surgical procedure in accordance with some embodiments.

FIG. 10 illustrates a flowchart illustrating a technique 1000 for tracking patient anatomy during a surgical procedure in accordance with some embodiments. In an example, operations of the technique 1000 may be performed by a processor, executing instructions stored in memory.

The technique 1000 includes an operation 1002 to capture a series of images of visible anatomy of a patient using a structured light camera. The structured light camera may be a camera affixed to an end effector of a robotic arm of a robotic surgical device. In an example, the robotic arm may be caused to move to keep visible anatomy within a visible region of the structured light camera. In an example, the structured light camera may include a laser rangefinder configured to output distance information from the structured light camera to the visible anatomy.

The technique 1000 includes an operation 1004 to receive a first image and a second image from the series of images. The series of images may be captured with a frequency of at least 60 Hz, in an example.

The technique 1000 includes a decision operation 1006 to determine whether visible anatomy has changed from the first image to the second image. Operation 1006 may include determining that a portion of anatomy of the patient visible in the first image is no longer visible in the second image.

The technique 1000 includes an operation 1008 to, in response to determining a change, cause the robotic arm to move. In response to determining that the visible anatomy has not changed, the technique 1000 may return to operation 1004. In an example, the technique 1000 may include registering a medical image to an image of the series of images using the distance information.

Figure 11:
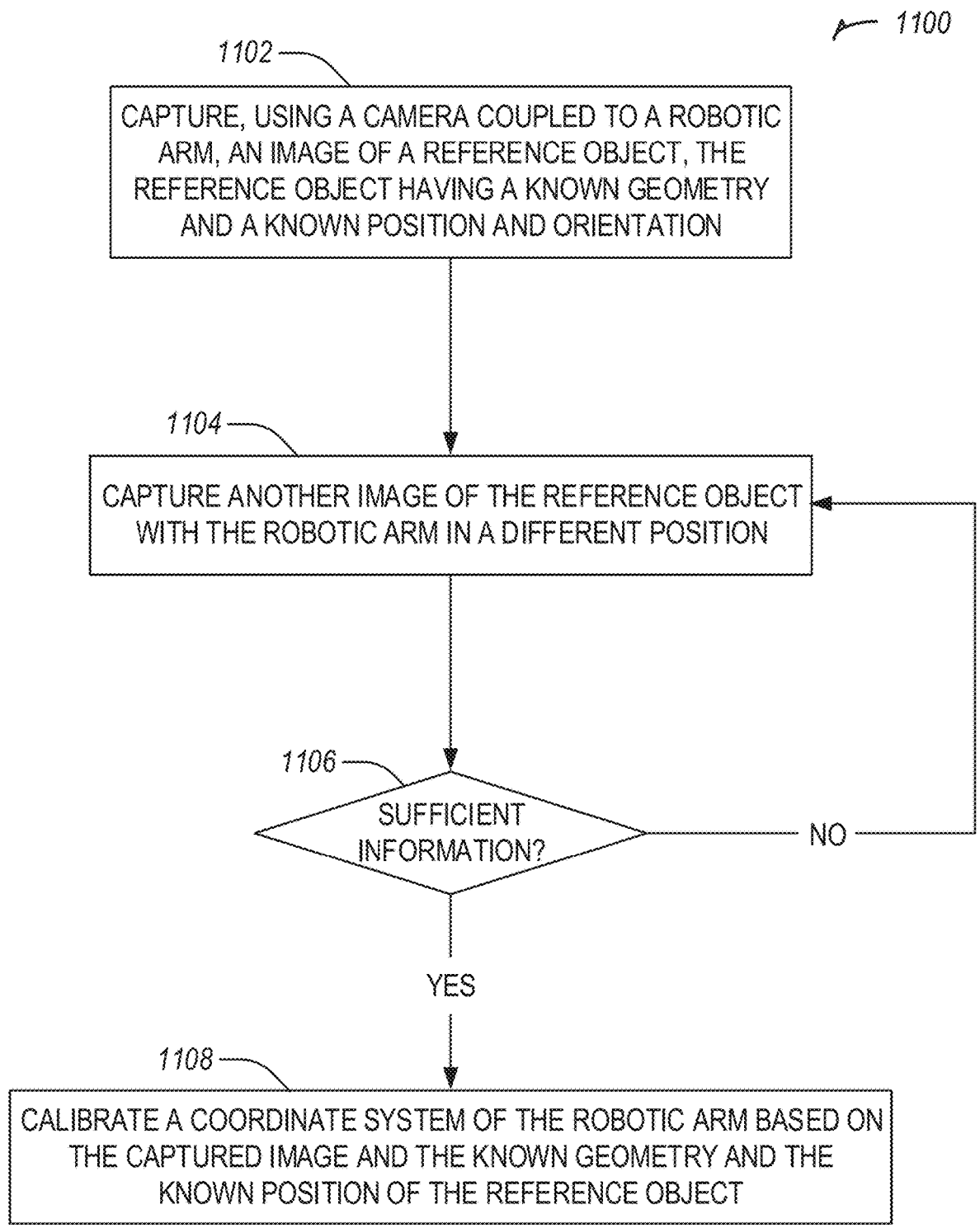
FIG. 11 illustrates a flowchart showing a technique for calibrating a camera system in accordance with some embodiments.

FIG. 11 illustrates a flowchart illustrating a technique 1100 for calibrating a camera system in accordance with some embodiments. In an example, operations of the technique 1100 may be performed by a processor, executing instructions stored in memory.

The technique 1100 includes an operation 1102 to capture, using a camera coupled to a robotic arm, an image of a reference object, the reference object having a known geometry and a known position and orientation. The robotic arm may be an arm affixed to a base of a robotic surgical device. The reference object may be affixed to or embedded in the base. The known position and orientation may be known with respect to the base or other aspect of the robotic surgical device.

The technique 1100 includes an operation 1104 to capture another image of the reference object with the robotic arm in a different position. The images may be captured by the camera, which may be affixed to or embedded in an end effector of the robotic arm.

The technique 1100 includes a decision operation 1106 to determine whether sufficient information has been captured to determine a relative location and orientation of the known object to the camera or a portion of the robotic arm. When sufficient information has been captured, the technique 1100 may proceed to operation 1108. When insufficient information has been captured, the technique 1100 may return to operation 1104 to capture another image of the reference object with the robotic arm in a different position (e.g., different from positions of the robotic arm when capturing previous images).

The technique 1100 includes an operation 1108 to calibrate a coordinate system of the robotic arm based on the captured image and the known geometry and the known position of the reference object.

Figure 12:
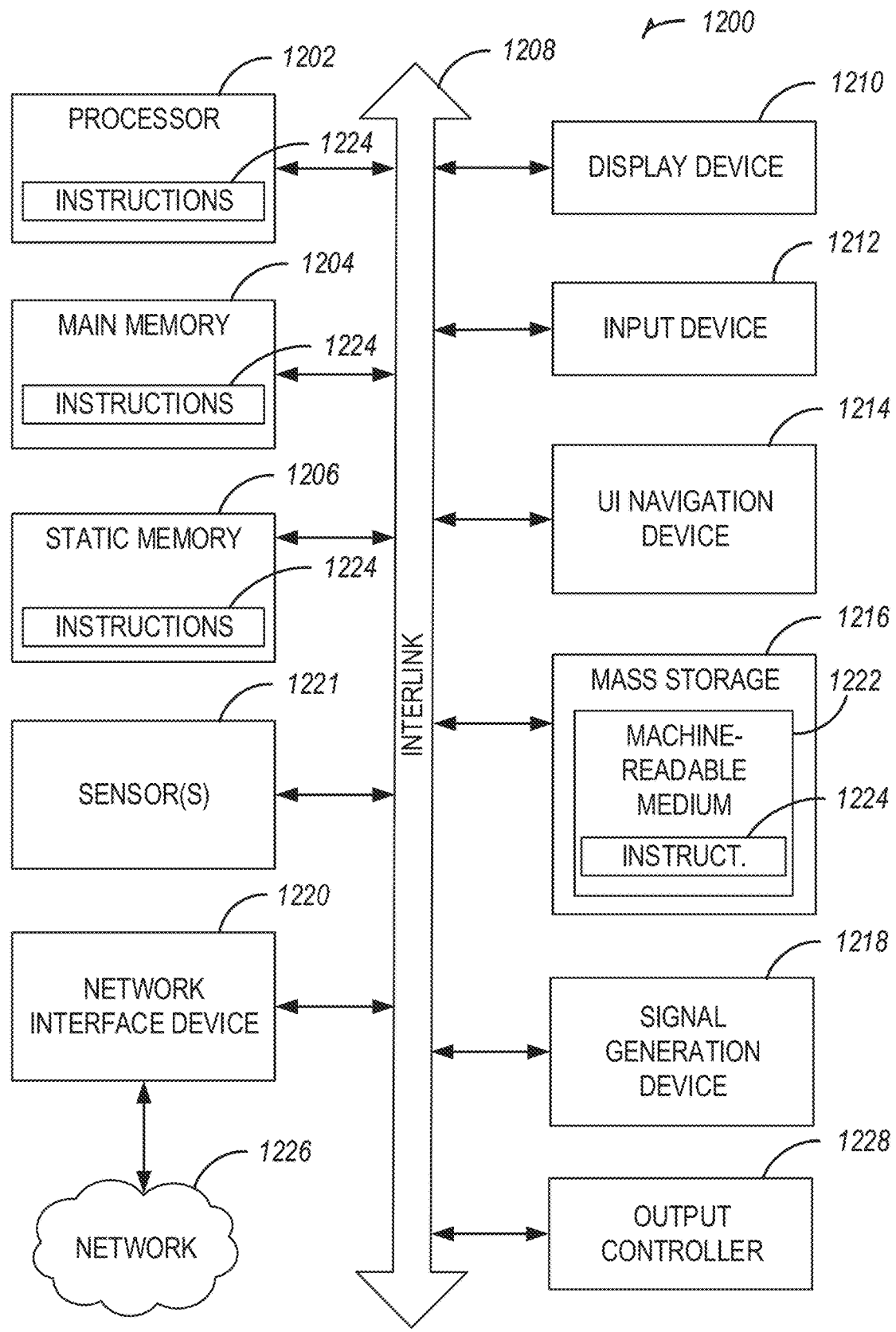
FIG. 12 illustrates a block diagram of an example machine upon which any one or more of the techniques discussed herein may perform in accordance with some embodiments.

FIG. 12 illustrates a block diagram of an example machine 1200 upon which any one or more of the techniques discussed herein may perform in accordance with some embodiments. In alternative embodiments, the machine 1200 may operate as a standalone device or may be connected (e.g., networked) to other machines. In a networked deployment, the machine 1200 may operate in the capacity of a server machine, a client machine, or both in server-client network environments. In an example, the machine 1200 may act as a peer machine in peer-to-peer (P2P) (or other distributed) network environment. The machine 1200 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1200 may include a hardware processor 1202 (e.g., a central processing unit (CPU), a graphics processing unit (GPU), a hardware processor core, or any combination thereof), a main memory 1204 and a static memory 1206, some or all of which may communicate with each other via an interlink (e.g., bus) 1208. The machine 1200 may further include a display unit 1210, an alphanumeric input device 1212 (e.g., a keyboard), and a user interface (UI) navigation device 1214 (e.g., a mouse). In an example, the display unit 1210, input device 1212 and UI navigation device 1214 may be a touch screen display. The machine 1200 may additionally include a storage device (e.g., drive unit) 1216, a signal generation device 1218 (e.g., a speaker), a network interface device 1220, and one or more sensors 1221, such as a global positioning system (GPS) sensor, compass, accelerometer, or other sensor. The machine 1200 may include an output controller 1228, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 1216 may include a machine readable medium 1222 on which is stored one or more sets of data structures or instructions 1224 (e.g., software) embodying or utilized by any one or more of the techniques or functions described herein. The instructions 1224 may also reside, completely or at least partially, within the main memory 1204, within static memory 1206, or within the hardware processor 1202 during execution thereof by the machine 1200. In an example, one or any combination of the hardware processor 1202, the main memory 1204, the static memory 1206, or the storage device 1216 may constitute machine readable media.

While the machine readable medium 1222 is illustrated as a single medium, the term "machine readable medium" may include a single medium or multiple media (e.g., a centralized or distributed database, and/or associated caches and servers) configured to store the one or more instructions 1224. The term "machine readable medium" may include any medium that is capable of storing, encoding, or carrying instructions for execution by the machine 1200 and that cause the machine 1200 to perform any one or more of the techniques of the present disclosure, or that is capable of storing, encoding or carrying data structures used by or associated with such instructions. Non-limiting machine-readable medium examples may include solid-state memories, and optical and magnetic media.

The instructions 1224 may further be transmitted or received over a communications network 1226 using a transmission medium via the network interface device 1220 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1220 may include one or more physical jacks (e.g., Ethernet, coaxial, or phone jacks) or one or more antennas to connect to the communications network 1226. In an example, the network interface device 1220 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1200, and includes digital or analog communications signals or other intangible medium to facilitate communication of such software.

Figure 13:
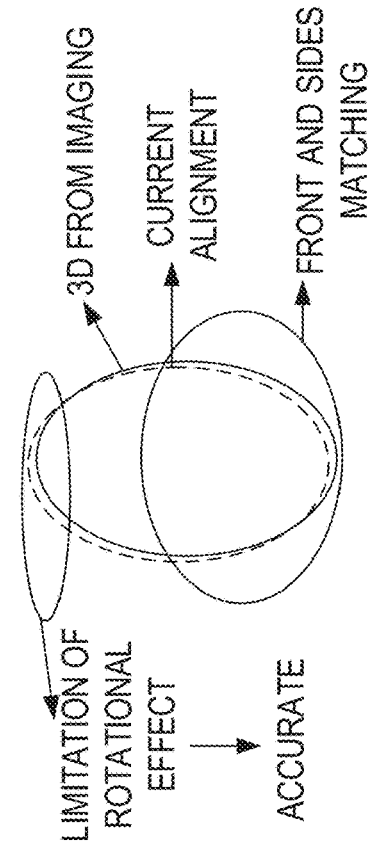
FIG. 13 illustrates a diagram showing structured light-based camera for 3D acquisition of a head in accordance with some embodiments.
Figure 13:
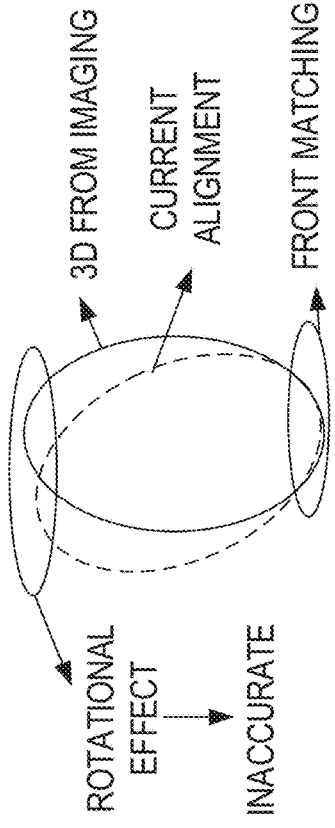

FIG. 13 illustrates a diagram showing a use of structured light-based camera for 3D acquisition of a head in accordance with some embodiments. The diagram includes a top view of a head out of alignment 1300A and a top view of a head in alignment 1300B, as determined from a structured light 3D image acquisition technique.

The technique may include identifying an alignment for a posterior approach for brain surgery. The structured light based camera may be used for a 3D acquisition of the front of the head and also the sides (e.g., left & right) of the head, providing a full 3D image or model of the top of the head. This full 3D dataset may be used to identify rotation of the head, to limit the rotational effect of the back of the head that may otherwise occur. For example, using a registration algorithm may identify a front match, but miss the rotational effect. Without the structured light image acquisition, only a partial 3D of the front of the face with a laser surface matching may miss this rotational effect. The rotational effect identification using the structured light image acquisition may provide an inaccuracy detection by matching the 3D acquired data by the structured light system to the 3D acquired by medical imaging (e.g., preoperative imaging) for the back of the head. By ensuring that the back of the head matches (e.g., is accurate as in 1300B), a posterior approach may be performed along a planned trajectory. However, when the back of the head is out of alignment (e.g., inaccurate as in 1300A), the planned trajectory may be inaccurate as well. A system may use the structured light images and comparison to medical imaging to output a visualization (e.g., on a user interface, displaying images such as those in 1300A or 1300B), an alert (e.g., a visual or audible alert), or the like to identify whether the head is rotationally accurate.

Each of these non-limiting examples may stand on its own, or may be combined in various permutations or combinations with one or more of the other examples.

Example 1 is a robotic surgical system comprising: a robotic arm connected to a base; an end effector connected to a distal end of the robotic arm; a camera affixed to or embedded in the end effector, the camera including a laser rangefinder configured to output distance information from the camera to patient anatomy, the distance information detected using a laser of the laser rangefinder; and processing circuitry configured to: determine whether the camera is within a particular range of the patient anatomy based on the distance information; and in response to determining that the camera is within the particular range, output an indication that the camera is within the particular range.

In Example 2, the subject matter of Example 1 includes, wherein the camera is configured to obtain a registration image of a patient after the camera is determined to be within the particular range, and wherein the processor is further configured to register a medical image to the registration image.

In Example 3, the subject matter of Examples 1-2 includes, wherein when the camera is not within the particular range, the processor is further configured to output an indication to move the robotic arm in a cooperative mode.

In Example 4, the subject matter of Examples 1-3 includes, wherein when the camera is not within the particular range, the processor is further configured to cause the robotic arm to move until the camera is determined to be within the particular range.

In Example 5, the subject matter of Examples 1-4 includes, wherein the camera is configured to track the patient anatomy after registration.

Example 6 is a robotic surgical system comprising: a robotic arm connected to a base; an end effector connected to a distal end of the robotic arm; a camera affixed to or embedded in the end effector; and processing circuitry configured to: launch an image acquisition and check procedure; determine whether an image captured by the camera includes, a particular portion of patient anatomy; in response to determining that the image includes the particular portion, identify a feature of the particular portion; and output an indication of where to move the robotic arm to cause the camera to move in a cooperative mode based on the identified feature.

In Example 7, the subject matter of Example 6 includes, wherein the image acquisition and check procedure includes iteratively checking images for the particular portion and features.

In Example 8, the subject matter of Examples 6-7 includes, wherein the particular portion is a head.

In Example 9, the subject matter of Examples 6-8 includes, wherein the camera is configured to obtain a registration image of a patient in response to the camera being determined to be within a particular range of the patient anatomy, and wherein the processor is further configured to register a medical image to the registration image.

Example 10 is a method comprising: using a laser rangefinder of a camera affixed to or embedded in an end effector connected to a distal end of a robotic arm, capturing distance information from the camera to patient anatomy; automatically causing the robotic arm to move to be within a particular range, based on the distance information; capturing an image using the camera; automatically registering the image to a medical image.

In Example 11, the subject matter of Example 10 includes, tracking the patient anatomy using the camera after registration.

Example 12 is a system comprising: a robotic surgical device including a base and a robotic arm affixed to the base; a reference object having a known geometry, the reference object affixed to or embedded in the base in a known position relative to the base; a camera affixed to or embedded in the end effector, the camera configured to capture an image of the reference object; a processor configured to calibrate a coordinate system of the robotic surgical device based on the captured image and the known geometry and the known position of the reference object.

In Example 13, the subject matter of Example 12 includes, wherein the robotic surgical device is configured to automatically place the camera in different positions to capture images of the reference object.

In Example 14, the subject matter of Examples 12-13 includes, wherein the camera includes a laser rangefinder configured to output distance information from the camera to the reference object, and wherein the processor is configured to use the distance information to calibrate the coordinate system.

In Example 15, the subject matter of Examples 12-14 includes, wherein after calibration, the processor is configured to use the camera to track patient anatomy.

In Example 16, the subject matter of Examples 12-15 includes, wherein the camera is configured to capture a plurality of images of the reference object with the robotic surgical device in a respective plurality of preregistered configurations.

Example 17 is a system comprising: a robotic surgical device including a robotic arm extending from a base; a structured light camera embedded on an end effector of the robotic arm, the structured light camera configured to capture a series of images of visible anatomy of a patient; a processor configured to: receive a first image and a second image from the series of images; determine whether the visible anatomy has changed from the first image to the second image; in response to determining a change, cause the robotic arm to move.

In Example 18, the subject matter of Example 17 includes, wherein the robotic arm is caused to move to keep the visible anatomy within a visible region of the camera.

In Example 19, the subject matter of Examples 17-18 includes, wherein determining the change includes determining that a portion of anatomy of the patient visible in the first image is no longer visible in the second image.

In Example 20, the subject matter of Examples 17-19 includes, wherein the series of images are captured with a frequency of at least 60 Hz.

In Example 21, the subject matter of Examples 17-20 includes, wherein the structured light camera includes a laser rangefinder configured to output distance information from the structured light camera to the visible anatomy, and wherein the processor is further configured to register a medical image to an image of the series of images using the distance information.

Example 22 is at least one machine-readable medium including instructions that, when executed by processing circuitry, cause the processing circuitry to perform operations to implement of any of Examples 1-21.

Example 23 is an apparatus comprising means to implement of any of Examples 1-21.

Example 24 is a system to implement of any of Examples 1-21.

Example 25 is a method to implement of any of Examples 1-21.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A robotic surgical system comprising:
a robotic arm connected to a base;
an end effector connected to a distal end of the robotic arm;
a camera affixed to or embedded in the end effector, the camera includes a laser rangefinder configured to output distance information from the camera to a reference object; and
processing circuitry configured to:
launch an image acquisition and check procedure;
use the distance information from the laser rangefinder to determine whether the camera is within a particular range of the reference object;
determine whether an image captured by the camera includes a particular portion of patient anatomy;
in response to determining that the image includes the particular portion, identify a feature of the particular portion; and
output an indication of where to move the robotic arm to cause the camera to move in a cooperative mode based on the identified feature.

2. The robotic surgical system of claim 1, wherein the image acquisition and check procedure includes iteratively checking images for the particular portion and features.

3. The robotic surgical system of claim 1, wherein the particular portion is a head.

4. The robotic surgical system of claim 1, wherein the camera is configured to obtain a registration image of a patient in response to the camera being determined to be within a particular range of the patient anatomy, and wherein the processing circuitry is further configured to register a medical image to the registration image.

5. The robotic surgical system of claim 1, wherein the camera is configured to obtain a registration image of a patient after the camera is determined to be within the particular range, and wherein the processing circuitry is further configured to register a medical image to the registration image.

6. The robotic surgical system of claim 5, wherein the camera is configured to track the particular portion of patient anatomy after the medical image is registered to the registration image.

7. A system comprising:
a robotic surgical device including a robotic arm extending from a base;
a structured light camera embedded on an end effector of the robotic arm and including a laser rangefinder, the structured light camera configured to capture a series of images of visible anatomy of a patient and the laser rangefinder configured to output distance information form the structured light camera to a reference object;
processing circuitry configured to:
receive a first image and a second image from the series of images;
use the distance information to determine whether the camera is within a particular range of the visible anatomy;
determine whether the visible anatomy has changed from the first image to the second image; and
in response to determining a change, cause the robotic arm to move.

8. The system of claim 7, wherein the robotic arm is caused to move to keep the visible anatomy within a visible region of the camera.

9. The system of claim 7, wherein determining the change includes determining that a portion of anatomy of the patient visible in the first image is no longer visible in the second image.

10. The system of claim 7, wherein the series of images are captured with a frequency of at least 60 Hz.

11. The system of claim 7, wherein the processing circuitry is further configured to register a medical image to an image of the series of images using the distance information after the camera is determined to be within the particular range.

12. The system of claim 7, wherein the structured light camera is further configured to capture an image of a reference object, and wherein the processing circuitry is further configured to calibrate a coordinate system of the robotic surgical device based on a captured image of the reference object.

13. A robotic surgical system comprising:
a robotic arm connected to a base;
an end effector connected to a distal end of the robotic arm;
a three-dimensional camera affixed to or embedded in the end effector, the three-dimensional camera including a laser rangefinder; and processing circuitry configured to:
calibrate the robotic surgical system to a surgical field using the three-dimensional camera;
use distance information from the laser rangefinder to determine whether the three-dimensional camera is within a particular range of anatomy of a patient;
register the anatomy of the patient to a medical image using the three-dimensional camera; and
track patient anatomy using output from the three-dimensional camera.

14. The robotic surgical system of claim 13, wherein the processing circuitry is further configured to track patient anatomy using the output from the three-dimensional camera by:
receiving a first image and a second image from a series of images;
determining whether visible anatomy has changed from the first image to the second image; and
in response to determining a change, cause the robotic arm to move.

15. The robotic surgical system of claim 14, wherein the robotic arm is caused to move to keep the visible anatomy within a visible region of the three-dimensional camera.

16. The robotic surgical system of claim 14, wherein determining the change includes determining that a portion of anatomy of the patient visible in the first image is no longer visible in the second image.

17. The robotic surgical system of claim 13, wherein the three-dimensional camera is configured to obtain a registration image of a patient after the three-dimensional camera is determined to be within the particular range, and wherein the processing circuitry is further configured to register the patient anatomy to the medical image based on the registration image.

* * * * *

UNITED STATES PATENT AND TRADEMARK OFFICE
CERTIFICATE OF CORRECTION

| | | |
|---|---|---|
| PATENT NO. | : 12,114,935 B2 | Page 1 of 1 |
| APPLICATION NO. | : 17/174068 | |
| DATED | : October 15, 2024 | |
| INVENTOR(S) | : Coiseur et al. | |

It is certified that error appears in the above-identified patent and that said Letters Patent is hereby corrected as shown below:

In the Claims

In Column 20, Line 30, in Claim 7, delete "form" and insert --from-- therefor

Signed and Sealed this
Seventeenth Day of December, 2024

Derrick Brent
*Acting Director of the United States Patent and Trademark Office*